(12) United States Patent
Berte' et al.

(10) Patent No.: US 8,003,718 B2
(45) Date of Patent: *Aug. 23, 2011

(54) OLIGOMERIC STERICALLY HINDERED AMINES AND THEIR USE AS POLYMER STABILISERS

(75) Inventors: Ferruccio Berte', Bergamo (IT); Massimo Magnoni, Bergamo (IT)

(73) Assignee: 3V SIGMA S.p.A., Milan (IT)

( * ) Notice: Subject to any disclaimer, the term of this patent is extended or adjusted under 35 U.S.C. 154(b) by 510 days.

This patent is subject to a terminal disclaimer.

(21) Appl. No.: 12/138,815

(22) Filed: Jun. 13, 2008

(65) Prior Publication Data

US 2009/0270536 A1    Oct. 29, 2009

(30) Foreign Application Priority Data

Apr. 23, 2008 (IT) ............................ MI2008A0739

(51) Int. Cl.
*C08K 5/3492* (2006.01)
*C07D 403/00* (2006.01)
*C09K 15/04* (2006.01)

(52) U.S. Cl. ......... 524/100; 252/399; 252/405; 544/212

(58) Field of Classification Search .................. 252/399, 252/405; 544/212; 524/100
See application file for complete search history.

(56) References Cited

U.S. PATENT DOCUMENTS

| | | | |
|---|---|---|---|
| 3,640,928 A | 2/1972 | Murayama et al. | |
| 4,038,280 A | 7/1977 | Randell et al. | |
| 4,086,204 A * | 4/1978 | Cassandrini et al. | ......... 524/101 |
| 4,104,248 A | 8/1978 | Cantatore | |
| 4,233,412 A | 11/1980 | Rody et al. | |
| 4,315,859 A | 2/1982 | Nikles et al. | |
| 4,325,863 A | 4/1982 | Hinsken et al. | |
| 4,331,586 A | 5/1982 | Hardy | |
| 4,338,244 A | 7/1982 | Hinsken et al. | |
| 4,433,145 A | 2/1984 | Wiezer et al. | |
| 4,477,615 A | 10/1984 | Raspanti et al. | |
| 4,530,950 A | 7/1985 | Raspanti et al. | |
| 4,692,486 A | 9/1987 | Gugumus | |
| 4,863,981 A | 9/1989 | Gugumus | |
| 5,021,485 A | 6/1991 | Gugumus | |
| 5,175,312 A | 12/1992 | Dubs et al. | |
| 5,216,052 A | 6/1993 | Nesvadba et al. | |
| 5,252,643 A | 10/1993 | Nesvadba et al. | |
| 7,713,444 B2 * | 5/2010 | Berte' et al. | ................. 252/405 |

FOREIGN PATENT DOCUMENTS

| | | |
|---|---|---|
| DE | 1 929 928 | 1/1970 |
| DE | 24 56 864 | 6/1975 |
| DE | 26 36 144 | 6/1977 |
| DE | 43 16 611 A1 | 11/1993 |
| DE | 43 16 622 A1 | 11/1993 |
| DE | 43 16 876 A1 | 11/1993 |
| EP | 0 589 839 B1 | 3/1994 |
| EP | 0 709 426 B2 | 5/1996 |
| EP | 0 728 806 82 | 8/1996 |

* cited by examiner

*Primary Examiner* — Kriellion A Sanders
(74) *Attorney, Agent, or Firm* — Arent Fox, LLP

(57) ABSTRACT

This invention relates to new polypiperidine compounds of general formula (I) which give different kinds of polymer materials, in particular polyolefins, high stability towards oxidative action and photodegradation.

The invention also relates to the processes used to prepare the compounds of formula (I).

10 Claims, No Drawings

OLIGOMERIC STERICALLY HINDERED AMINES AND THEIR USE AS POLYMER STABILISERS

The present invention relates to polypiperidine compounds which give different kinds of polymer materials, in particular polyolefins, high stability towards oxidative action and photodegradation.

The invention also relates to the processes used to prepare the compounds according to the invention.

INTRODUCTION

Polymers are known to be subject to deterioration caused by heat, light and oxygen; these factors cause loss of their mechanical properties, discolouring and other adverse effects.

In order to stabilise polymer materials, mainly towards the UV radiation in sunlight, various classes of compounds have been proposed, such as benzophenones and benzotriazoles. The stability which these compounds give polymers is acceptable, but insufficient to meet practical needs, especially in the case of fibres, films and raffia based on olefin polymers.

The polyalkylpiperidine derivatives commonly called HALS (hindered amine light stabilisers) are far more effective, and there are numerous patents relating to them. See, for example, U.S. Pat. No. 4,530,950, DE 1,929,928, U.S. Pat. No. 3,640,928, U.S. Pat. No. 4,477,615, U.S. Pat. No. 4,233,412, U.S. Pat. No. 4,331,586, DE 2,636,144, DE 2,456,864, U.S. Pat. No. 4,315,859, U.S. Pat. No. 4,104,248, U.S. Pat. No. 4,086,204 and U.S. Pat. No. 4,038,280.

Synergic effects are also claimed for mixtures of HALS, e.g. in U.S. Pat. No. 4,692,486, U.S. Pat. No. 4,863,981, U.S. Pat. No. 5,021,485, EP 0709426 and EP 0728806.

DESCRIPTION OF THE INVENTION

It has now been found that the following oligomers of general formula (I) are particularly effective:

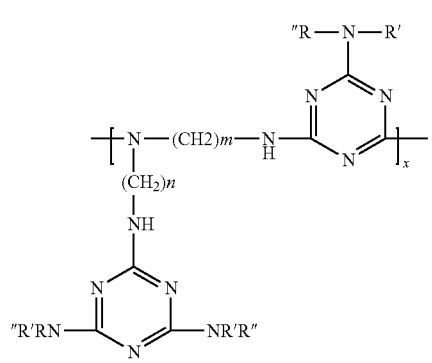

wherein x is between 2 and 10;

parameters m and n take the values 2 to 8 and may have different values in the individual monomer units constituting the oligomer mixture;

groups R' and R", which are the same or different, are straight or branched $C_2$-$C_8$ alkyl groups, or the group of formula (V)

where R'''=H or straight or branched $C_1$-$C_4$ alkyl group

Formula I shown above represents a mixture of different oligomers characterised by different values and meanings for x, n, m, R', R".

The compounds of formula (I) can be obtained by a process which involves reacting an amine of general formula (II)

$$NH_2-(CH_2)_m-NH-(CH_2)_n-NH_2 \qquad (II)$$

where m and n are as defined above, with a derivative of formula (III)

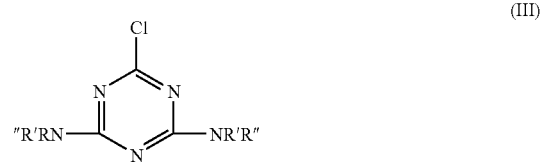

where R' and R", which are the same or different, represent straight or branched $C_2$-$C_8$ alkyl groups, preferably $C_4$, or the group of formula (V)

with R'''=H or straight or branched $C_1$-$C_4$ alkyl group and then, having obtained the intermediate, consisting of a mixture of compounds of formula general (VI) and (VI)' shown below

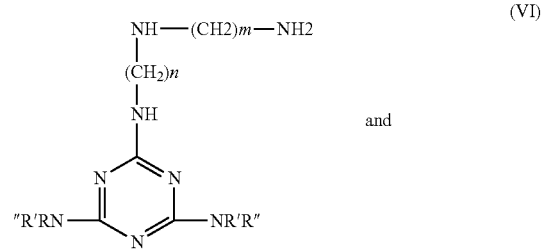

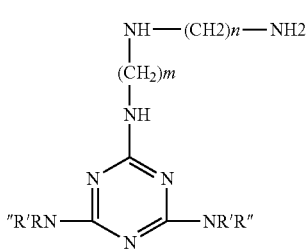

(VI)′ where m, n, R' and R" are as defined above,
with compounds of formula (IV):

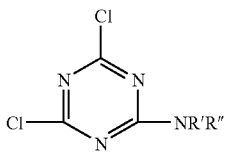

(IV)

where R', R" have the meanings described above.

Indexes m, n are preferably from 2 to 3, and differ from one another in each amine of formula (II).

The terminal groups of the molecule of formula (I) may be H, OH, OR with R=alkyl or an amine group, in particular an amine group derived from formula (VI) or (VI').

Any residual amine groups can be further reacted, if required, with compounds of formula (VII)

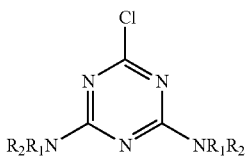

formula (VII)

wherein $R_1$ and $R_2$, which are the same or different, represent H or a straight or branched $C_1$-$C_4$ alkyl group or the group of formula (V).

A further object of the invention is the use of compounds of formula (I), alone or mixed with other monomeric, polymeric or macromolecular HALS, as stabilisers for polymers, in particular for polyolefin polymers.

According to the present invention, polymers comprise polyethylene, polypropylene, polystyrene, polybutadiene, polyisoprene and their copolymers, polyvinyl chloride, polivinylidene chloride and their copolymers, polyvinyl acetate and its copolymers, in particular with ethylene; polyesters such as polyethylene terephthalate; polyamides such as Nylon 6 and 6.6; and polyurethanes.

The compounds of the invention can be incorporated in polymers by any known method for mixing additives and polymer materials, for example by:
 mixing with the polymer, which may be in the form of powder or granulate, in a suitable mixer or extruder;
 addition in the form of a solution or suspension in a suitable solvent, and subsequent removal of the solvent from the polymer, which may be in the form of a powder, granulate or suspension, after thorough mixing;
 addition to the polymer during its preparation, for example during the last stage of preparation.

The compounds of formula (I) can also be added together with other types of stabilisers and additives generally used in the art, such as monomeric, polymeric or macromolecular HALS in general; antioxidants based on phenols, amines or phosphites; UV radiation absorbers based on benzophenones or benzotriazoles; nickel-based stabilisers; plasticisers, lubricants, antistatic agents, flame retardants, corrosion inhibitors, metal deactivators and mineral fillers such as titanium dioxide, aluminium oxide and the like.

Examples of said additives are:

1. Antioxidants 1.1. Alkylated phenols, for example 2,6-di-tert-butyl-4-methylphenol; 2-tert-butyl-4,6-di-methylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(α-methylcyclohexyl)-4,6-dimethyl-phenol; 2,6-dioctadecyl-4-methylphenol; 2,4,6-tricyclohexyl-phenol; 2,6-di-tert-butyl-4-methoxymethyl-phenol; linear or branched nonylphenols, for example, 2,6-dinonyl-4-methylphenol; 2,4-dimethyl-6-(1'-methylundecyl)-phenol; 2,4-dimethyl-6-(1'-heptadecyl)phenol; and mixtures thereof.

1.2. Alkylthiomethylphenols, for example 2,4-dioctylthiomethyl-6-tert-butylphenol; 2,4-dioctylthiomethyl-6-methylphenol; 2,4-dioctylthiomethyl-6-ethylphenol; 2,6-di-dodecylthiomethyl-4-nonylphenol.

1.3. Hydroquinones and alkylated hydroquinones, for example 2,6-di-tert-butyl-4-methoxy-phenol; 2,5-di-tert-butylhydroquinone; 2,5-di-tert-amylhydroquinone; 2,6-diphenyl-4-octadecyloxyphenol; 2,6-di-tert-butyl-hydroquinone; 2,5-di-tert-butyl-4-hydroxyanisole; 3,5-di-tert-butyl-4-hydroxyanisole; 3,5-di-tert-butyl-4-hydroxyphenyl stearate; bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2, 2'-thiobis-(6-tert-butyl-4-methylphenol); 2,2'-thiobis(4-octylphenol); 4,4-thiobis-(6-tert-butyl-3-methylphenol); 4,4'-thiobis-(6-tert-butyl-2-methylphenol); 4,4'-bis-(2,6-dimethyl-4-hydroxyphenyl)disulphide.

1.6. Alkylidenebisphenols, for example 2, 2'-methylenebis(6-tert-butyl-4-methylphenol); 2,2'-methylenebis(6-tert-butyl-4-ethylphenol); 2,2'-methylenebis[4-methyl-6-(α-methylcyclohexyl)-phenol]; 2,2'-methylene bis-(4-methyl-6-cyclohexylphenol); 2,2'-methylenebis(6-nonyl-4-methylphenol); 2,2'-methylenebis-(4,6-di-tert-butylphenol); 2,2'-ethylidenebis-(4,6-di-tert-butyl-phenol); 2,2'-ethylidenebis-(6-tert-butyl-4-isobutylphenol); 2,2'-methylenebis[6-(α-methylbenzyl)-4-nonylphenol]; 2,2'-methylenebis[6-(α,α-dimethylbenzyl)-4-nonylphenol]; 4,4'-methylenebis(2,6-di-tert-butylphenol); 4,4'-methylenebis-(6-tert-butyl-2-methylphenol); 1,1-bis(5-tert-butyl-4-hydroxy-2-methylphenyl)-butane; 2,6-bis(3-tert-butyl-5-methyl-2-hydroxybenzyl)-4-methyl phenol; 1,1,3-tris(5-tert-butyl-4-hydroxy-2-methyl phenyl)-butane; 1,1-bis(5-tert-butyl-4-hydroxy-2-methyl-phenyl)-3-n-dodecyl-mercaptobutane; ethylene glycol bis[3,3-bis(3'-tert-butyl-4'-hydroxyphenyl)butyrate]; bis-[2-(3'-tert-butyl-2'-hydroxy-5'-methyl benzyl)-6-tert-butyl-4-methylphenyl] terephthalate; bis(3-tert-butyl-4-hydroxy-5-methyl-phenyl) dicyclopentadiene; 1,1-bis-(3,5-dimethyl-2-hydroxyphenyl) butane; 2,2-bis-(3,5-di-tert-butyl-4-hydroxyphenyl)-propane; 2,2-bis-(5-tert-butyl-4-hydroxy-2-methylphenyl)-4-n-dodecylmercaptobutane; 1,1,5,5-tetra-(5-tert-butyl-4-hydroxy-2-methylphenyl)-pentane.

1.7. O-, N- and S-benzyl compounds, for example 3, 5,3', 5'-tetra-tert-butyl-4,4'-dihydroxy-di-benzylether, octadecyl- 4-hydroxy-3,5-dimethylbenzyl-mercaptoacetate, tridecyl-4-hydroxy-3,5-di-tert-butylbenzyl mercaptoacetate, tris(3,5-di-tert-butyl-4-hydroxybenzyl)amine, bis(4-tert-butyl-3-hydroxy-2,6-dimethylbenzyl)dithioterephtalate, bis(3,5-di-tert-butyl-4-hydroxy-benzyl)-disulphide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)-malonate, bis-[4-(1,1,3,3-tetramethylbutyl)-phenyl]-2,2-bis(3,5-di-tert-butyl-4-hydroxybenzyl) malonate.

1.9. Aromatic hydroxybenzyl compounds, for example 1,3,5-tris-(3,5-di-tert-butyl-4-hydroxy-benzyl)-2,4,6-trimethylbenzene, 1,4-bis(3,5-di-tert-butyl-4-hydroxybenzyl)-2,3,5,6-tetramethylbenzene, 2,4,6-tris-(3,5-di-tert-butyl-4-hydroxybenzyl)phenol.

1.10. Triazine compounds, for example 2,4-bis-(octylmercapto)-6-(3,5-di-tert-butyl-4-hydroxyanilino)-1,3,5-triazine, 2-octylmercapto-4,6-bis-(3,5-di-tert-butyl-4-hydroxyanilino)-1,3,5-triazine, 2-octylmercapto-4,6-bis-(3,5-di-tert-butyl-4-hydroxyphenoxy)-1,3,5-triazine, 2,4,6-tris-(3,5-di-tert-butyl-4-hydroxyphenoxy)-1,3,5-triazine, 1,3,5-tris-(3,5-di-tert-butyl-4-hydroxy-benzyl) isocyanurate, 1,3,5-tris-(4-tert-butyl-3-hydroxy-2,6-dimethylbenzyl)-isocyanurate, 2,4,6-tris-(3,5-di-tert-butyl-4-hydroxyphenylethyl)-1,3,5-triazine, 1,3,5-tris-(3,5-di-tert-butyl-4-hydroxyphenylpropionyl)-hexahydro-1,3,5-triazine, 1,3,5-tris-(3,5-dicyclohexyl-4-hydroxybenzyl) isocyanurate.

1.11. Benzylphosphonates, for example dimethyl-2,5-di-tert-butyl-4-hydroxybenzylphosphonate, diethyl-3,5-di-tert-butyl-4-hydroxybenzyl-phosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl-N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, iso-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, iso-octanol, octadecanol, 1,6-hexane-diol, 1,9-nonanediol, ethylene glycol, 1,2-propanediol, neopentyl glycol, thiodiethylene glycol, diethylene glycol, triethylene glycol, pentaerythritol, tris-(hydroxyethyl) isocyanurate, N,N'-bis-(hydroxyethyl)oxamide, 3-thiaundecanol, 3-thiapentadecanol, trimethyl-hexanediol, trimethylolpropane, 4-hydroxymethyl-1-phospha-2,6,7-trioxabicyclo[2.2.2)octane.

1.15. Esters of β-(3-,5-dicyclohexyl-4-hydroxyphenyl) propionic acid with mono- or polyhydric alcohols, e.g. with methanol, ethanol, n-octanol, iso-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, n-octanol, iso-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethyl-hexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis-(3,5-di-tert-butyl-4-hydroxyphenylpropionyl)-hexamethylene-diamide, N,N'-bis-(3,5-di-tert-butyl-4-hydroxy-phenylpropionyl)-trimethylene-diamide, N,N'-bis-(3,5-di-tert-butyl-4-hydroxyphenylpropionyl)-hydrazide, N,N'-bis(2-(3-[3,5-di-tert-butyl-4-hydroxyphenyl]propionyloxy)ethyl]oxamide.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylene-diamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulphamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis-(4-methoxyphenyl)-amine, 2,6-di-tert-butyl-4-dimethylamino-methyl-phenol, 2,4'-diaminodiphenylmethane, 4,4-diamino-diphenyl-methane, N,N,N',N'-tetramethyl-4,4'-diaminodiphenylmethane, 1,2-bis[(2-methylphenyl)amino]ethane, 1,2-bis(phenylamino)propane, (o-tolyl)-biguanide, bis[4-(1',3'-dimethylbutyl)phenyl] amine, tert-octyl-N-phenyl-1-naphthylamine, mixtures of mono- and dialkylated tert-butyl/tert-octyldiphenylamines, mixtures of dialkylated nonyldiphenyl-amines, mixtures of mono- and dialkylated dodecyldiphenylamines, mixtures of mono- and dialkylated isopro-pyl/isohexyldiphenylamines, mixtures of mono- and dialkylated tert-butyldiphenylamines, 2,3-dihydro-3,3-dimethyl-4H-1,4-benzothiazine, phenothiazine, mixtures of mono- and dialkylated tert-butyl/tert-octylphenothiazines, mixtures of mono- and dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis-(2,2,6,6-tetramethylpiperid-4-yl)-sebacate, 2,2,6,6-tetramethylpiperidin-4-one, 2,2,6,6-tetramethyl piperidin-4-ol.

2. UV Adsorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)benzotriazole, 2-(2'-hydroxy-5'-(1,1,3,3-tetramethyl butyl)phenyl)benzotriazole, 2-(3',5'-di-tert-butyl-2'-hydroxyphenyl)-5-chloro-benzotriazole, 2-(3'-tertbutyl-2'-hydroxy-5'-methyl-phenyl)-5-chloro-benzotriazole, 2-(3'-sec-butyl-5'-tert-butyl-2'-hydroxy-phenyl)benzotriazole, 2-(2'-hydroxy-4'-octyloxyphenyl)benzotriazole, 2-(3',5'-di-tert-amyl-2'-hydroxyphenyl)-benzotriazole, 2-(3',5'-bis-(α,α-dimethyl-benzyl)-2'-hydroxy-phenyl)-benzotriazole, 2-(3'-tert-butyl-5'-[2-(2-ethylhexyl-oxy)-carbonylethyl]-2'-hydroxyphenyl)-5-chloro-benzotriazole, 2-(3'-tert-butyl-2-hydroxy-5'-(2-octyloxycarbonyl-ethyl)phenyl)-5-chloro-benzotriazole, 2-(3'-tert-butyl-2'-hydroxy-5'-(2-methoxycarbonyl)-ethyl)-phenyl)-5-chloro-benzotriazole, 2-(3'-tert-butyl-2'-hydroxy-5'-(2-methoxy-carbonyl-ethyl)phenyl benzotriazole, 2-(3'-tert-butyl-2'-hydroxy-5'-(2-octyloxycarbonyl-ethyl)-phenyl)benzotriazole, 2-(3'-tert-butyl-5'-[2-(2-ethylhexyloxy)-carbonylethyl]-2'-hydroxy-phenyl)benzotriazole, 2-(3'-dodecyl-2'-hydroxy-5'-methylphenyl)-benzotriazole, 2-(3'-tert-butyl-2'-hydroxy-5'-(2-iso-octyloxy-carbonyl-ethyl)-phenylbenzotriazole, 2,2'-methylene-bis-[4-(1,1,3,3-tetra-methylbutyl)-6-benzotriazole-2-yl-phenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$— where R may be 3'-tert-butyl-4'-hydroxy-5'-2H-benzotriazol-2-yl-phenyl; 2-[2'-hydroxy-3'-(α,α-dimethyl-benzyl)-5'-(1,1,3,3-tetramethyl-butyl)-phenyl]benzotriazole; 2-[2'-hydroxy-3'-(1,1,3,3-tetramethyl-butyl)-5'-(α,α-dimethyl-benzyl)-phenyl]-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2,4'-trihydroxy and 2-hydroxy-4,4'-dimethoxy derivatives.

2.3. Esters of substituted and unsubstituted benzoic acids, for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butyl phenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl (α-cyano-β,β-diphenylacrylate, isooctyl α-cyano-β,β-diphenylacrylate, methyl α-carbomethoxycinnamate, methyl-α-cyano-β-methyl-p-methoxy-cinnamate, butyl α-cyano-β-methyl-p-methoxycinnamate, methyl-α-carbomethoxy-p-methoxycinnamate and N-(β-carbomethoxy-α-cyanovinyl)-2-methylindoline.

2.5. Nickel compounds, for example nickel complexes of 2,2'-thio-bis-[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl esters, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, such as: the condensate of 2,4-dichloro-6-(4-n-butylamino-2,2,6,6-tetramethyl-4-piperidyl)-1,3,5-triazine with the condensate of 2-chloro-4,6-bis-(4-n-butylamino-2,2,6,6-tetramethyl-4-piperidyl)-1,3,5-triazine with 1,2 bis(3-aminopropylamino) ethane, CAS RN=136504-96-6; bis(2,2,6,6-tetramethyl-4-piperidyl)sebacate, CAS RN=52829-07-9; bis(2,2,6,6-tetramethyl-4-piperidyl)succinate; bis(1,2,2,6,6-pentamethyl-4-piperidyl)sebacate, CAS RN=41556-26-7; (1,2,2,6,6-penta-methyl-4-piperidyl)methyl sebacate, CAS RN=82919-37-7; bis(1-octyloxy-2,2,6,6-tetramethyl-4-piperidyl)sebacate, CAS RN=129757-67-1; bis (1,2,2,6,6-pentamethyl-4-piperidyl) n-butyl-3,5-di-ter-butyl-4-hydroxybenzyl-malonate; the condensate of 1-(2-hydroxyethyl)-2,2,6,6-tetramethyl-4-hydroxypiperadine with succinic acid, CAS RN=65447-77-0; cyclic or straight-chain condensates of N,N'-bis-(2,2,6,6-tetramethyl-4-piperidyl)-hexamethylenediamine with 4-tert-octylamino-2,6-dichloro-1,3,5-triazine, CAS RN=71878-19-8; tris(2,2,6,6-tetramethyl-4-piperidyl)nitrilotriacetate; tetra(2,2,6,6-tetramethyl-4-piperidyl)-1,2,3,4-butane-tetra-carboxylate; 1.1'-(1,2-ethanediyl)-bis(3,3,5,5-tetramethylpiperazinone); 4-benzoyl-2,2,6,6-tetramethylpiperidine; 4-stearyloxy-2,2,6,6-tetramethylpiperidine, CAS RN=167078-06-0; bis(1,2,2,6,6-pentamethyl-4-piperidyl)-2-n-butyl-2-(hydroxy-3,5-di-tert-butylbenzyl)malonate, CAS RN=63843-89-0; 3-n-octyl-7,7,9,9-tetramethyl-1,3,8-triazaspiro(4,5)decane-2,4-dione; bis(1-octyloxy-2,2,6,6-tetramethyl piperidyl)sebacate; bis(1-octyloxy-2,2,6,6-tetramethyl-piperidyl)succinate; cyclic or straight-chain condensates of N,N'-bis-(2,2,6,6-tetramethyl-4-piperidyl) hexamethylenediamine with 4-morpholine-2,6-dichloro-1,3,5-triazine, CAS RN=82451-48-7; cyclic or straight-chain condensates of N,N'-bis-(1,2,2,6,6-pentamethyl-4-piperidyl)-hexamethylene-diamine with 4-morpholine-2,6-dichloro-1,3,5-triazine, CAS RN=193098-40-7; the condensate of 2-chlorine-4,6-bis(4-n-butylamino-2,2,6,6-tetramethyl-piperidyl)-1,3,5-triazine with 1,2-bis(3-aminopropylamino)ethane; the condensate of 2-chloro-4,6-bis(4-n-butylamino-1,2,2,6,6-pentamethyl-piperidyl)-1,3,5-triazine with 1,2-bis(3-aminopropylamino)ethane, CAS RN=106990-43-6; 8-acetyl-3-dodecyl-7,7,9,9-tetramethyl-1,3,8-triazaspiro-(4,5)decane-2,4-dione; 3-dodecyl-1-(2,2,6,6-tetramethyl-4-piperidyl)-pyrrolidine-2,5-dione; 3-dodecyl-1-(1,2,2,6,6-pentamethyl-4-piperidyl)-pyrrolidine-2,5-dione; mixture of 4-hexadecyloxy- and 4-octadecyloxy-2,2,6,6-tetramethylpiperidine; condensate of N,N'-bis-(2,2,6,6-tetramethyl-4-piperidyl)hexamethylenediamine with 4-cyclohexylamino-2,6-dichloro-1,3,5-triazine; N-(2,2,6,6-tetramethyl-4-piperidyl)n-dodecylsuccinimide; 2-undecyl-7,7,9,9-tetramethyl-1-oxo-3,8-diazo-4-oxo-spiro(4,5)decane; condensate of 7,7,9,9-tetramethyl-2-cycloundecyl-1-oxo-3,8-diazo-4-oxo-spiro(4,5)decane with epichlorhydrin; 1,1-bis (1,2,2,6,6-pentamethyl?-4-piperidyloxycarbonyl)-2-(4-methoxyphenyl)ethene; N,N'-bis-formyl-N,N'-bis(2,2,6,6-tetramethyl-4-piperidyl)hexamethylenediamine; diester of 4-methoxy-methylene-malonic acid with 1,2,2,6,6-pentamethyl-4-hydroxypiperadine; poly(methylpropyl-3-oxy-4-(2,2,6,6-tetramethyl-4-piperidyl))-siloxane; reaction product of maleic acid/alpha-olefin copolymer with 2,2,6,6-tetramethyl-4-aminopiperidine or 1,2,2,6,6-pentamethyl-4-aminopiperidine; condensate of 2-chloro-4,6-bis-(4-n-butylamino-1-cyclohexyloxy-2,2,6,6-tetramethylpiperidinyl)-1,3,5-triazine with 1,2-bis-(3-amino-propylamino)-ethane; condensate of 1,6-hexanediamine-bis(2,2,6,6-tetramethyl-4-piperidyl)- with the condensate of 2,4,6-trichloro-1,3,5-triazine with di-n-butylamine and N-butyl-2,2,6,6-tetramethyl-4-piperidinamine, CAS RN=192268-64-7; derivatives of 7-oxa-3,20-diaza-dispiro-(5.1.11.2)-heneicosanone identified by CAS RN 64338-16-5; 85099-51-0; 85099-50-9; 202483-55-4; reaction product of 2,2,6,6-tetramethyl-4-piperidine with the polymer obtainable by copolymerisation of maleic anhydride with alkenes C20-24, CAS RN=152261-33-1; products disclosed in EP 782994.

2.7. Oxamides, for example 4, 4'-dioctyloxyoxanilide, 2,2'-diethoxyoxanilide, 2,2'-dioctyloxy-5,5'-di-tertbutyl-oxanilide, 2,2'-didodecyl-oxy-5,5'-di-tertbutyl-oxanilide, 2-ethoxy-2'-ethyloxanilide, N,N'-bis(3-dimethyl-aminopropyl)oxanilide, 2-ethoxy-2'-ethyl-5,4'-di-tert-oxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methyl phenyl)-1,3,5-triazine, 2-(2-hydroxy-4-dodecyloxyphenyl)-4,6-bis-(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propoxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-(2-hydroxy-4-[3-(2-ethylhexyl-1-oxy)-2-hydroxy-propyloxy]phenyl)-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxalanilide, isophthaloyl dihydrazide, sebacoyl bisphenylhydrazide, N,N'-diacetyladipoyldihydrazide, N,N'-bis(salicyl-oyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl)-phosphite; diisodecyl pentaerythritol diphosphite, bis(2,4-di-tert-butylphenyl)-pentaerythritol diphosphite, bis-(2,6-di-tertbutyl-4-methylphenyl)-pentaerythritol-diphosphite, diisodecyl pentaerythritol diphosphite, bis(2,4-di-tert-butyl-6-methylphenyl)pentaerythritol diphosphite, bis(2,4,6-tris (tert-butylphenyl)pentaerythritol diphosphite, tristearyl sorbitol triphosphite, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2-idyl)phosphite], 2-ethylhexyl-(3,3',5,5'-tetra-tert-butyl-1,1'-biphenyl-2,2'-idyl)-phosphite, tetra-(2,4-di-tert-butylphenyl) 4,4'-biphenylene diphosphonite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or stearyl thiodipropionate.

8. Peroxide scavengers, for example thiodipropionic acid esters: for example the lauryl, stearyl, myristyl or tridecyl alcohols, mercaptobenzimidazole or the zinc salt of 2-mercapto-benzimidazole, zinc dibutyldithiocarbamate, dioctadecyl disulphide, pentaerythritol tetrakis(p-dodecyl mercapto) propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony or zinc salts of pyrocatechol.

11. Nucleating agents, for example, inorganic substances such as talcum; metal oxides such as titanium dioxide or magnesium oxide, phosphates, carbonates or sulphates of alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as anionic copolymers.

12. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoethoxy)-phenyl]-5,7-di-tert-butyl-benzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy] phenyl)-benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(2,3-di-methyl-phenyl)-5,7-di-tert-butyl-benzofuran-2-one.

13. Fillers and reinforcing agents, for example, calcium carbonate, silicates, glass fibres, asbestos, talc, kaolin, mica, barium sulphate, metal oxides and hydroxides, carbon black, graphite, wood flour and flours of fibres or other natural products; synthetic fibres.

14. Other additives, for example, plasticisers, lubricants, emulsifiers, pigments, rheology additives, catalysts, flow-control agents, optical brighteners, flameproofing agents, antistatic agents and blowing agents.

The amount of compounds of formula (I) required for effective stabilisation of the polymer depends on a number of factors, such as the type and characteristics of the polymer, its intended use, the intensity of the radiation, and the duration of the likely exposure. A amount of 0.01 to 5% by weight of the polymer, preferably 0.1 to 1.0%, is usually sufficient.

The following examples illustrate the invention in greater detail.

PREPARATION EXAMPLES

Example 1

Preparation Example 0.1 Mole of cyanuryl chloride are dissolved in 100 ml of toluene. 0.2 moles of N-(2,2,6,6-tetramethyl-4-piperidinyl)- butylamine and 0.1 moles of sodium carbonate are added under stirring, heating to 80° C., and maintaining said temperature for 3 hours still under stirring. Then the organic layer is washed twice with 200 ml of distilled water to remove the salts.

0.1 Mole of 3-(2-aminoethylamine)propylamine, corresponding to an amine of general formula (II) with m=2 and n=3, are added to the toluene solution obtained, containing 0.1 moles of a compound of general formula (III), with R'=n-butyl and R"=2,2,6,6-tetramethyl-4-piperidine residue; acidity is neutralised with the equivalent amount of alkali, the solution is heated to reflux, and the water formed is distilled off. When distillation of the water has finished, the mixture is cooled to 90° C. and the organic layer is washed twice with 200 ml of distilled water.

The toluene layer, containing a substantially equimolecular mixture of compounds of general formula (VI), where m=2 and n=3, and (VI)', where m=3 and n=2, is reacted with 0.09 moles of 2,4-dichloro-6-N-(2,2,6,6-tetramethyl-4-piperidinyl)-butylamine, previously obtained by dripping 0.09 moles of N-(2,2,6,6-tetramethyl-4-piperidinyl)-butylamine at the temperature of 15-20° C. into 0.09 moles of cyanuryl chloride dissolved in 100 ml of toluene, followed by neutralisation with the equivalent amount of alkali, by cascade heating for 5 hours, in the presence of 0.2 moles of sodium carbonate, and removal of the reaction water by distillation.

At the end of the reaction, cool to 80° C. and wash twice with 200 ml of distilled water.

After filtration of any undissolved parts, the solution obtained by distillation of solvent under vacuum is dried, to obtain 84 grams of a mixture of oligomers of formula (I) wherein indexes m and n have the values 2 and 3 (HALS 1).

Example 2

Preparation Example 0.1 Mole of cyanuryl chloride are dissolved in 100 ml of toluene. 0.2 Moles of N-(2,2,6,6-tetramethyl-4-piperidinyl)-butylamine and 0.1 moles of sodium carbonate are added under stirring, heating to 80° C. and maintaining said temperature for 3 hours, still under stirring. Then the organic layer is washed twice with 200 ml of distilled water to remove the salts.

0.1 Moles of N-(3-aminopropyl)-1,4-diaminobutane (CAS RN 124-20-9), corresponding to an amine of general formula (II), with m=3 and n=4, are added to the toluene solution obtained, containing 0.1 moles of a compound of general formula (III), with R'=n-butyl and R"=2,2,6,6-tetramethyl-4-piperidine residue; acidity is neutralised with the equivalent amount of alkali, the solution is heated to reflux, and the water formed is distilled off. When distillation of the water has finished, the mixture is cooled to 90° C. and the organic layer is washed twice with 200 ml of distilled water.

The toluene layer, containing a substantially equimolecular mixture of compounds of general formula (VI), where m=3 and n=4, and (VI)', where m=4 and n=2, is reacted with 0.09 moles of 2,4-dichloro-6-N-(2,2,6,6-tetramethyl-4-piperidinyl)-butylamine, previously obtained by dripping 0.09 moles of N-(2,2,6,6-tetramethyl-4-piperidinyl)-butylamine at the temperature of 15-20° C. into 0.09 moles of cyanuryl chloride dissolved in 100 ml of toluene, followed by neutralisation with the equivalent amount of alkali by cascade heating for 5 hours, in the presence of 0.2 moles of sodium carbonate, and removal of the reaction water by distillation.

At the end of the reaction, the mixture is cooled to 80° C. and washed twice with 200 ml of distilled water.

After filtration of any undissolved parts, the solution obtained by distillation of solvent under vacuum is dried, to obtain 86 grams of a mixture of oligomers of formula (I) wherein indexes m and n have the values 3 and 4 (HALS 2).

Example 3

Comparison Preparation Example 0.1 Mole of cyanuryl chloride are dissolved in 100 ml of toluene. 0.2 Moles of N-(2,2,6,6-tetramethyl-4-piperidinyl)-butylamine and 0.1 moles of sodium carbonate are added under stirring, heating to 80° C., and maintaining said temperature for 3 hours, still under stirring. Then the organic layer is washed twice with 200 ml of distilled water to remove the salts.

0.1 Moles of diethylenetriamine, corresponding to an amine of general formula (II) with m=n=2, are added to the toluene solution obtained, containing 0.1 moles of a compound of general formula (III), with R'=n-butyl and R"=2,2,6,6-tetramethyl-4-piperidine residue; acidity is neutralised with the equivalent amount of alkali, the solution is heated to reflux and the water formed is distilled off. When distillation of the water has finished, the mixture is cooled to 90° C. and the organic layer is washed twice with 200 ml of distilled water.

The toluene layer, containing the compound of general formula (VI), where m=n=2, is reacted with 0.09 moles of 2,4-dichloro-6-N-(2,2,6,6-tetramethyl-4-piperidinyl)-butylamine, previously obtained by dripping 0.09 moles of N-(2,2,6,6-tetramethyl-4-piperidinyl)-butylamine at the temperature of 15-20° C. into 0.09 moles of cyanuryl chloride dissolved in 100 ml of toluene, followed by neutralisation with the equivalent amount of alkali by cascade heating for 5 hours, in the presence of 0.2 moles of sodium carbonate, and removal of the reaction water by distillation. At the end of the reaction, the mixture is cooled to 80° C. and washed twice with 200 ml of distilled water.

After filtration of any undissolved parts, the solution obtained by distillation of solvent under vacuum is dried, to obtain 86.5 grams of a mixture of oligomers of formula (I) wherein indexes m and n have the value 2 (HALS 3).

APPLICATION EXAMPLES

In the examples below, HALS 1 indicates the compound described in preparation example 1, HALS 2 the compound described in preparation example 2, and HALS 3 the compound described in preparation example 3.

Application Example 1

Light Stabilisation of Polypropylene Fibre 1000 parts of unstabilised polypropylene homopolymer powder (fluidity index: approx. 23 g/'10' at 230° C.-2.16 kP) is mixed in a laboratory mixer with 0.75 parts of calcium stearate, 0.50 parts of tris-(2,4-di-ter-butyl-phenyl) phosphite, 0.50 parts of 1,3,5-tris-(3,5-di-ter-butyl-4-hydroxybenzyl) isocyanurate and 3 parts of HALS stabiliser as shown in Table 1.

The dry mixture is extruded in a laboratory extruder at 230° C. and granulated.

The granulate is transformed into multifilament yarn by spinning with a laboratory extruder at a maximum temperature of 260° C., to obtain a multifilament yarn with a titre of 480/60 dtex.

The yarn is exposed in a WOM according to ISO 4892. The light resistance of the yarn is monitored by periodic sampling; the modulus of elasticity of the samples is tested with a UTS test.

The parameter used to compare the light resistance of the samples is $t_{50}$, defined as "time of exposure in WOM, expressed in hours, at a UTS amounting to 50% of the initial value".

The experimental results obtained are summarised in Table 1.

TABLE 1

Light stability of multifilament yarn PP 480/60 dtex

| Stabilisation | $t_{50}$ hours |
|---|---|
| Without light stabiliser | 300 |
| 0.30% HALS 1 | 1430 |
| 0.30% HALS 3 | 1255 |

Application Example 2

Light Stabilisation of High-Density Polyethylene Raffia 1000 parts of unstabilised high-density polyethylene (fluidity index: approx. 2 g/'10' at 190° C.-2.16 kP) are mixed in a laboratory mixer with 0.30 parts of 1,3,5-tris-(3,5-di-ter-butyl-4-hydroxybenzyl) isocyanurate and 1 part of HALS stabiliser as shown in Table 2.

The dry mixture is extruded in a laboratory extruder at 230° C. and granulated.

The granulate is then transformed into raffia (thickness 50 μm) by extrusion at a maximum temperature of 230° C. and 1:5 stretching in a specific plant.

The raffia is exposed in a WOM according to ISO 4892. The light resistance of the raffia is monitored by periodic sampling; the modulus of elasticity of the samples is tested with a UTS test.

The parameter used to compare the light resistance of the samples is $t_{50}$, defined as "time of exposure in WOM, expressed in hours, at a UTS amounting to 50% of the initial value".

The experimental results obtained are summarised in Table 2.

TABLE 2

Light stability of HDPE raffia with a thickness of 50 μm

| Stabilisation | $t_{50}$ hours WOM |
|---|---|
| Without light stabilisation | 510 |
| 0.10% HALS 2 | 3100 |
| 0.10% HALS 3 | 2700 |

Application Example 3

Light Stabilisation of LDPE Film 1000 parts of unstabilised low-density polyethylene (fluidity index: approx. 0.60 g/'10' at 190° C.-2.16 kP) are mixed in a laboratory mixer with 0.30 parts of n-octadecyl-3-(3',5'-di-ter-butyl-4-hydroxyphenyl)-propionate and 1.50 parts of HALS stabilisers as shown in Table 3.

The dry mixture is extruded in a laboratory extruder at 230° C. and granulated.

The granulate is then transformed into film with a final thickness of approx. 150 μm by extrusion and bubble film making with a laboratory extruder fitted with a rotary head, at a maximum temperature of 230° C.

Specimens taken from said film are mounted on supports and exposed in a WOM according to ISO 4892.

The light resistance of the product is monitored by periodic sampling; the carbonyl index of the samples is tested with FT-IR measurements.

The parameter used to compare the light resistance of the samples is to, defined as "time of exposure in WOM, expressed in hours, required for the carbonyl index to increase to the value of 0.10".

The experimental results obtained are summarised in Table 3.

TABLE 3

Light stability of LDPE blown film with a thickness of 150 μm

| Stabilisation | $t_{0.10}$ hours WOM |
|---|---|
| Without light stabilisation | 250 |
| 0.15% HALS 1 | 4200 |
| 0.15% HALS 3 | 3950 |

The invention claimed is:

1. Oligomer compounds of general formula (I)

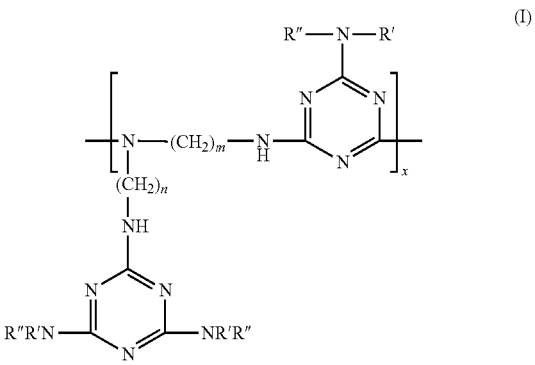

wherein x is between 2 and 10;
parameters m and n take the values 2 to 8 and may have different values in the individual monomer units constituting the oligomer mixture;
groups R' and R", which are the same or different, are straight or branched $C_2$-$C_8$ alkyl groups, or the group of formula (V)

with R'''=H or straight or branched $C_1$-$C_4$ alkyl group.

2. Compounds as claimed in claim 1, wherein m and n have the values 2 and 3.

3. Compounds as claimed in claim 1 or 2, wherein R' is butyl.

4. Compounds as claimed in claims 1 to 3, wherein R" is the group of formula (V)

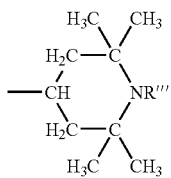

(V)

where R'" is as defined above.

5. Method for obtaining the compounds of formula (I), which involves:

(a) reacting amines of formula (II)

(II)

where m and n are different from one another and may take values from 2 to 8, with compounds of formula (III)

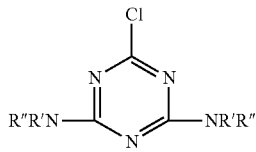

(III)

where R' and R" have the meanings indicated above, and then (b) reacting the intermediate obtained at stage (a) with compounds of formula (IV)

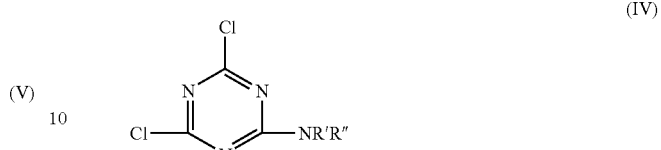

(IV)

wherein R' and R" have the meanings indicated above.

6. Method as claimed in claim 5, wherein the molar ratio between the amine of formula (II) and the compound of formula (III) is between 0.9 and 1.1.

7. Polymers stabilised with 0.01% to 5% by weight of the compounds claimed in claim 1.

8. Polyolefins as claimed in claim 7.

9. Method for stabilising the polymers claimed in claims 7 and 8, which involves adding 0.01% to 5% by weight of the compounds of formula (I) by incorporation at any stage of their production.

10. Mixtures of stabilisers based on sterically hindered amines which include the compounds of formula (I).

* * * * *